(12) United States Patent
Iwata et al.

(10) Patent No.: US 10,906,898 B2
(45) Date of Patent: Feb. 2, 2021

(54) COCRYSTAL

(71) Applicant: TAKEDA PHARMACEUTICAL COMPANY LIMITED, Osaka (JP)

(72) Inventors: Kentaro Iwata, Kanagawa (JP); Yukihiro Ikeda, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 188 days.

(21) Appl. No.: 16/074,339

(22) PCT Filed: Jan. 31, 2017

(86) PCT No.: PCT/JP2017/003453
§ 371 (c)(1),
(2) Date: Jul. 31, 2018

(87) PCT Pub. No.: WO2017/135259
PCT Pub. Date: Aug. 10, 2017

(65) Prior Publication Data
US 2020/0048245 A1    Feb. 13, 2020

(30) Foreign Application Priority Data

Feb. 1, 2016 (JP) ................................. 2016-017099

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
None
See application file for complete search history.

(56) References Cited

U.S. PATENT DOCUMENTS 8,217,176 B2 * 7/2012 Oguro ................. C07D 471/14
546/114
2009/0227561 A1   9/2009 Fujii et al.

FOREIGN PATENT DOCUMENTS

EP      2247588 A2    11/2010
WO      2009107850     9/2009

OTHER PUBLICATIONS

Abramov, Y.A., et al., "Rational Coformer or Solvent Selection for Pharmaceutical Cocrystallization or Desolvation", Journal of Pharmaceutical Sciences, 2012, vol. 101, No. 10, pp. 3687-3697.
Abstracts of The Academy of Pharmaceutical Science and Technology, Japan, 31st Annual Meeting, May 19-21, 2016, Japanese Language.
Abstracts of The Academy of Pharmaceutical Science and Technology, Japan, 31st Annual Meeting, May 19-21, 2016, English Translation.
Amidon, G.L., et al., "A Theoretical Basis for a Biopharmaceutic Drug Classification: The Correlation of the in Vitro Drug Product Dissolution and in the Vivo Bioavailability", Pharmaceutical Research, 1995, vol. 12, No. 3, pp. 413-420.
Hilfiker, R., et al., "Relevance of Solid-state Properties for Pharmaceutical Products", Polymorphism: In the Pharmaceutical Industry, Wiley-VCH Verlag GmbH & Co. KGaA (2006), pp. 1-3.
International Search Report for PCT/JP2017/003453 dated Apr. 4, 2017, English Translation.
Iwata, K., et al., "Cocrystallization Enhanced TAK-441 Aqueous Solubility and Suppressed High Solvatomorphism", Crystal Growth & Design, 2016, vol. 16, No. 8, pp. 4599-4606.
Iwata, K., et al., "Solid Form Selection of Highly Solvating TAK-441 Exhibiting Solvate—Trapping Polymorphism", Crystal Growth & Design, 2014, vol. 14, No. 7, pp. 3335-3342.
Kojima, T., et al., "Application of in situ Raman Microscopy to Cocrystal Screening", Journal of Pharmaceutical Machinery and Engineering, 2012, vol. 21, No. 2, (whole No. 77), pp. 23 to 28.
Ohashi, T., et al., "Discovery of the investigational drug TAK-441, a pyrrolo[3,2-c]pyridine derivative, as a highly potent and orally active hedgehog signaling inhibitor: Modification of the core skeleton for improved solubility," Bioorganic & Medicinal Chemistry, 20 (2012), pp. 5507-5517.
Qiao, N., et al., "Pharmaceutical cocrystals: An overview", International Journal of Pharmaceutics, 2011, vol. 419, Nos. 1-2, pp. 1-11.
Schultheiss, N., et al., "Pharmaceutical Cocrystals and Their Physicochemical Properties," Crystal Growth & Design, 2009, vol. 9, No. 6, pp. 2950-2967.
Shan, N., et al., "The role of cocrystals in pharmaceutical science", Drug Discovery Today, 2008, vol. 13, Nos. 9/10, pp. 440-446.
Office Action from corresponding Eurasian Application No. 201891736/28, dated Apr. 30, 2019.
Extended European Search Report for EP Appln. No. 17747415.2, dated Aug. 19, 2019.
Elder, D., et al., "Use of pharmaceutical salts and cocrystals to address the issue of poor solubility", International Journal of Pharmaceutics, vol. 453, No. 1 (Nov. 24, 2012), pp. 88-100.
Office Action for corresponding Chinese Application No. 201780018561.6, dated Jun. 3, 2020 (includes English translation).

* cited by examiner

*Primary Examiner* — Zinna Northington Davis
(74) *Attorney, Agent, or Firm* — Barnes & Thornburg LLP

(57) ABSTRACT

Improving the solubility of an organic compound. A cocrystal of (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and (2) L-malic acid or L-tartaric acid.

12 Claims, 11 Drawing Sheets

COCRYSTAL

CROSS-REFERENCE TO RELATED APPLICATIONS

This application is a 35 U.S.C. § 371 United States National Phase Application of, and claims priority to, PCT Application No.: PCT/JP2017/003453, filed Jan. 31, 2017, which claims priority to Japanese Application Serial No. 2016-017099, filed Feb. 1, 2016. The entire contents of the aforesaid applications are incorporated by reference herein in their entirety.

TECHNICAL FIELD

The present invention relates to a pharmaceutical composition containing a cocrystal.

BACKGROUND OF THE INVENTION

For absorption of a drug from the intestinal tract, dissolution process or membrane permeation process is the rate-determining step (non-patent document 1). In the case of a poorly soluble drug, the dissolution process is often the rate-determining step, and the bioavailability of the drug is expected to increase by improving the solubility.

It is known that solvates including hydrates and crystal polymorphs each have different physicochemical properties of crystals including solubility. Controlling to a single crystal form is important for keeping the quality of pharmaceutical products constant (non-patent document 2).

"Cocrystal" generally refers to a multicomponent crystal containing intermolecular interactions in which components constituting the cocrystal are linked by an interaction other than an ionic bond (non-patent document 3).

It is known that 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide has a Smo inhibitory action and is useful as a prophylactic or therapeutic agent for cancer (patent document 1).

It has been suggested that the membrane permeability of this drug is good (non-patent document 4). To increase the bioavailability, therefore, it is necessary to improve the solubility of the drug. This drug forms solvates with many organic solvents, and various polymorphisms are induced from the solvates (non-patent document 5), which makes production with control of the crystal form difficult.

DOCUMENT LIST

Patent Document patent document 1: JP-B-4719317

Non-Patent Documents non-patent document 1: Gordon L. Amidon et al., "A Theoretical Basis for a Biopharmaceutic Drug Classification: The Correlation of in Vitro Drug Product Dissolution and in Vivo Bioavailability", Pharmaceutical Research 12 (1995) 413-420 non-patent document 2: Rolf Hilfiker "Polymorphism: In the Pharmaceutical Industry", WILEY-VCH Verlag GmbH & Co. KGaA (2006)

non-patent document 3: Goud, N. R. et al., "The role of cocrystals in pharmaceutical science", Drug Discovery Today, Vol. 13 (2008) 440-446 non-patent document 4: Ohashi, T. et al., "Discovery of the investigational drug TAK-441, a pyrrolo[3,2-c]pyridine derivative, as a highly potent and orally active hedgehog signaling inhibitor: Modification of the core skeleton for improved solubility", Bioorganic & Medicinal Chemistry, 20, 2012. 5507-5517 non-patent document 5: Iwata, K. et al., "Solid Form Selection of Highly Solvating TAK-441 Exhibiting Solvate-Trapping Polymorphism", Crystal Growth & Design, 14, 2012. 3335-3342

SUMMARY OF THE INVENTION

Problems to be Solved by the Invention

The present invention aims to facilitate control of the crystal form, which is important for the quality of pharmaceutical products, in production by cocrystallizing 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide useful as a prophylactic or therapeutic agent for cancer, which achieves higher solubility than conventional stable crystals composed of single drug component, and further suppressing formation of a solvate.

Means of Solving the Problems

The present inventors have conducted intensive studies in an attempt to achieve the above-mentioned object and could obtain a cocrystal that improves solubility of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and does not easily form a solvate. Based on the finding, the present invention is as described below.

[1] A cocrystal of (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and (2) L-malic acid or L-tartaric acid;

[2] the cocrystal of [1] that is a cocrystal of (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and (2) L-malic acid;

[3] the cocrystal of [2], showing a powder X-ray diffraction pattern having characteristic peaks at the lattice spacing (d) of 11.7±0.2, 10.0±0.2 and 8.6±0.2 angstroms by powder X-ray diffraction;

[4] the cocrystal of [1] that is a cocrystal of (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and (2) L-tartaric acid;

[5] the cocrystal of [4], showing a powder X-ray diffraction pattern having characteristic peaks at the lattice spacing (d) of 12.0±0.2, 10.1±0.2 and 8.7±0.2 angstroms by powder X-ray diffraction;

[6] a medicament comprising the cocrystal of [1];

[7] the medicament of [6] that is a Smo inhibitor;

[8] the medicament of [6] that is a prophylactic and/or therapeutic agent for cancer;

[9] a method for inhibiting Smo in a mammal, comprising administering an effective amount of the cocrystal of [1] to the mammal;

[10] a method for preventing and/or treating cancer in a mammal, comprising administering an effective amount of the cocrystal of [1] to the mammal;

[11] the cocrystal of [1] for use in the prophylaxis and/or treatment of cancer; and

[12] use of the cocrystal of [1] in the production of a prophylactic and/or therapeutic agent for cancer.

Effect of the Invention

A cocrystal of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide having superior solubility and suppressing easy formation of a solvate may be provided.

DETAILED DESCRIPTION OF THE INVENTION

Figure 1:
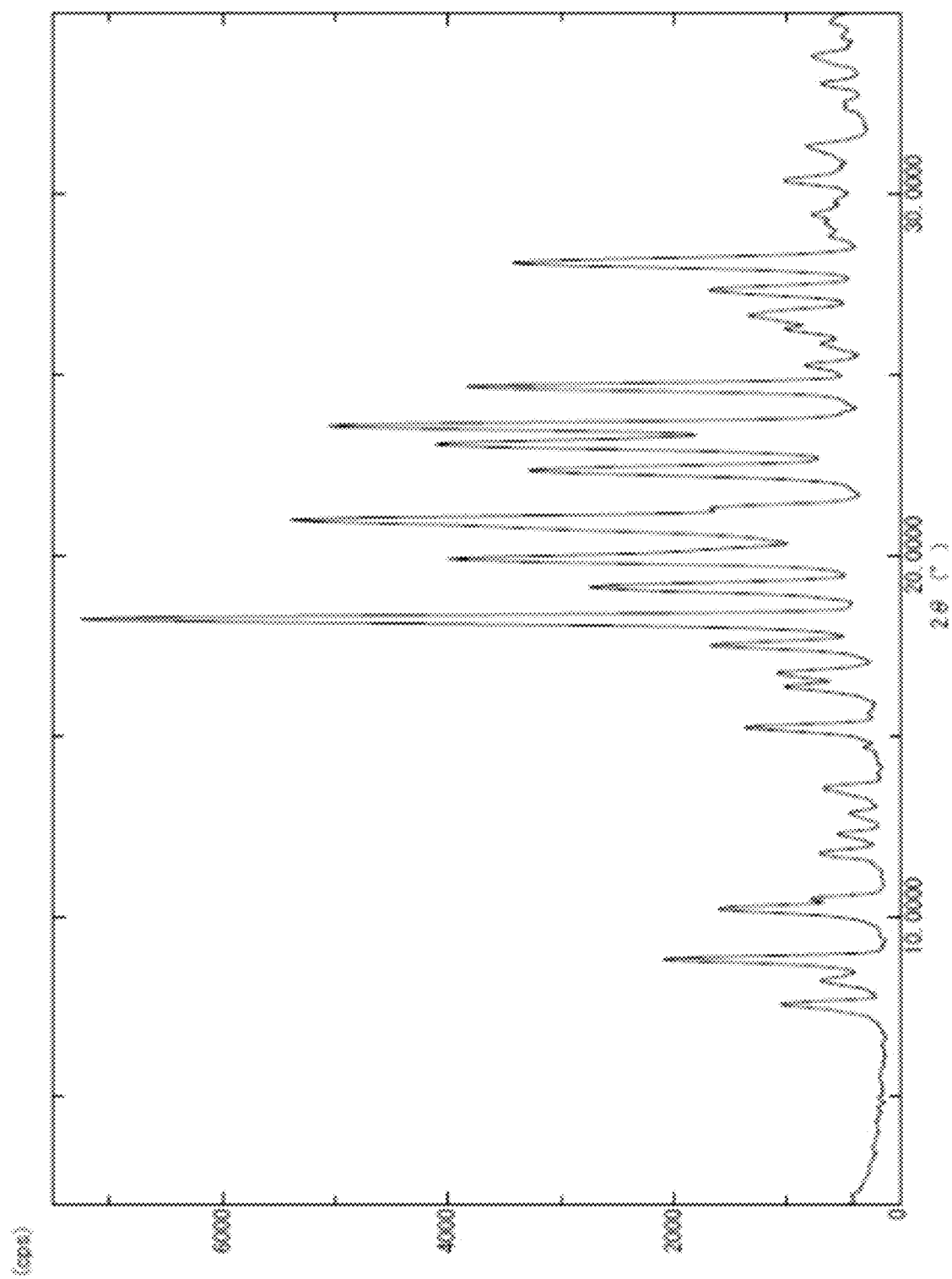
FIG. 1 shows a powder X-ray diffraction pattern of a cocrystal of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-malic acid.

The present invention provides a cocrystal of (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and (2) L-malic acid or L-tartaric acid (hereinafter to be referred to as "the cocrystal of the present invention").

In the present invention, the "cocrystal" means a crystal in which an organic compound and a cocrystal former constituting the cocrystal are bonded by an intermolecular interaction other than an ionic bond (e.g., hydrogen bond, van der Waals force, pi-pi bond etc.). Whether a certain compound is a cocrystal or a salt whose constituent components are bound by an ionic bond can be confirmed by single crystal X-ray diffraction method, infrared spectroscopy or the like (Schultheiss N. et al., "Pharmaceutical Cocrystals and Their Physicochemical Properties", Crystal Growth & Design, 9, 2009. 2950-2967).

6-Ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide can be produced by, for example, a known method such as the one described in patent document 1.

Examples of the malic acid that forms a cocrystal with 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide include L-malic acid, D-malic acid and DL-malic acid. Of these, L-malic acid is preferable.

As a cocrystal of (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and (2) L-malic acid, a cocrystal showing a powder X-ray diffraction pattern having characteristic peaks at the lattice spacing (d) of 11.7±0.2, 10.0±0.2 and 8.6±0.2 angstroms by powder X-ray diffraction is preferable.

As a cocrystal of (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and (2) L-malic acid, a cocrystal showing a powder X-ray diffraction pattern having characteristic peaks at the lattice spacing (d) of 11.7±0.2, 10.0±0.2, 8.6±0.2, 5.8±0.2 and 4.9±0.2 angstroms by powder X-ray diffraction is preferable.

Furthermore, as the above-mentioned cocrystal, a cocrystal showing a powder X-ray diffraction pattern having characteristic peaks at the lattice spacing (d) of 11.7±0.2, 10.7±0.2, 10.0±0.2, 8.6±0.2, 8.4±0.2, 5.8±0.2 and 4.9±0.2 angstroms by powder X-ray diffraction, a cocrystal showing a powder X-ray diffraction pattern having characteristic peaks at the lattice spacing (d) of 11.7±0.2, 10.7±0.2, 10.0±0.2, 8.6±0.2, 8.4±0.2, 7.5±0.2, 7.2±0.2, 5.8±0.2 and 4.9±0.2 angstroms by powder X-ray diffraction, or a cocrystal showing a powder X-ray diffraction pattern having characteristic peaks at the lattice spacing (d) of 11.7±0.2, 10.7±0.2, 10.0±0.2, 8.6±0.2, 8.4±0.2, 7.5±0.2, 7.2±0.2, 5.8±0.2, 4.9±0.2, 4.5±0.2 and 4.2±0.2 angstroms by powder X-ray diffraction is preferable.

Examples of the tartaric acid forming a cocrystal with 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide include L-tartaric acid, D-tartaric acid, DL-tartaric acid and meso-tartaric acid. Of these, L-tartaric acid is preferable.

As a cocrystal of (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and (2) L-tartaric acid, a cocrystal showing a powder X-ray diffraction pattern having characteristic peaks at the lattice spacing (d) of 12.0±0.2, 10.1±0.2 and 8.7±0.2 angstroms by powder X-ray diffraction is preferable.

As a cocrystal of (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and (2) L-tartaric acid, a cocrystal showing a powder X-ray diffraction pattern having characteristic peaks at the lattice spacing (d) of 12.0±0.2, 10.1±0.2, 8.7±0.2, 5.9±0.2 and 4.9±0.2 angstroms by powder X-ray diffraction is preferable.

Furthermore, as the above-mentioned cocrystal, a cocrystal showing a powder X-ray diffraction pattern having characteristic peaks at the lattice spacing (d) of 12.0±0.2, 11.0±0.2, 10.1±0.2, 8.4±0.2, 8.7±0.2, 5.9±0.2 and 4.9±0.2 angstroms by powder X-ray diffraction, a cocrystal showing a powder X-ray diffraction pattern having characteristic peaks at the lattice spacing (d) of 12.0±0.2, 11.0±0.2, 10.1±0.2, 8.4±0.2, 8.7±0.2, 7.6±0.2, 7.3±0.2, 5.9±0.2 and 4.9±0.2 angstroms by powder X-ray diffraction, or a cocrystal showing a powder X-ray diffraction pattern having characteristic peaks at the lattice spacing (d) of 12.0±0.2, 11.0±0.2, 10.1±0.2, 8.4±0.2, 8.7±0.2, 7.6±0.2, 7.3±0.2, 5.9±0.2, 4.9±0.2, 4.7±0.2 and 4.5±0.2 angstroms by powder X-ray diffraction is preferable.

Cocrystals can be produced, for example, from an organic compound and a cocrystal former by, for example, a known method such as the method described in Qiao, N et al., "Pharmaceutical cocrystals: An overview", International Journal of Pharmaceutics, 419, 2011. 1-11 (e.g., slow cooling method from a solution, poor solvent addition method, solvent evaporation method, slurry aging method, co-pulverization method, melting method etc.) or a combination of the principles thereof.

The cocrystal of the present invention interacts, for example, with human Smo protein and changes the steric structure thereof, whereby formation of a complex with a protein involved in the signal transduction in the cytoplasm is inhibited and the Hedgehog signal transduction system is inhibited. Alternatively, the cocrystal of the present invention interacts with human Smo protein and directly inhibits formation of a complex of human Smo protein with a protein involved in the Hedgehog signal transduction system in the cytoplasm, whereby the Hedgehog signal transduction system is inhibited. Alternatively, the cocrystal of the present invention interacts with a site of an Smo protein, for example, phosphorylation site and the like, which is modified by a protein involved in the Hedgehog signal transduction system, whereby modification such as phosphorylation of Smo and the like is inhibited and the Hedgehog signal transduction system is inhibited.

Therefore, the cocrystal of the present invention is useful as a Smo inhibitor for mammals (e.g., mouse, rat, hamster, rabbit, cat, dog, bovine, sheep, monkey, human, etc.). The cocrystal of the present invention is used as a pharmaceutical agent such as an agent for the prophylaxis or treatment of diseases possibly influenced by Smo, for example, cancer [e.g., colorectal cancer (e.g., colon cancer, rectal cancer, anal cancer, familial colorectal cancer, hereditary nonpolyposis colorectal cancer, gastrointestinal stromal tumor, etc.), lung cancer (e.g., non-small cell lung cancer, small cell lung cancer, malignant mesothelioma, etc.), mesothelioma, pancreatic cancer (e.g., pancreatic duct cancer, pancreatic endocrine tumor, etc.), pharyngeal cancer, laryngeal cancer, esophageal cancer, gastric cancer (e.g., papillary adenocarcinoma, mucinous adenocarcinoma, adenosquamous cancer, etc.), duodenal cancer, small intestinal cancer, breast cancer (e.g., invasive ductal breast carcinoma, ductal cancer in situ, inflammatory breast cancer, etc.), ovarian cancer (e.g., ovarian epithelial cancer, extragonadal germ cell tumor, ovarian germ cell tumor, ovarian low malignant potential tumor, etc.), testicular tumor, prostate cancer (e.g., hormone-dependent prostate cancer, non-hormone dependent prostate cancer, etc.), liver cancer (e.g., hepatocellular carcinoma, primary liver cancer, extrahepatic bile duct cancer, etc.), thyroid cancer (e.g., medullary thyroid cancer, etc.), kidney cancer (e.g., renal cell carcinoma, renal pelvis and ureter transitional cell cancer, etc.), uterus cancer (e.g., cervical cancer, cancer of uterine body, uterine sarcoma, etc.), brain tumor (e.g., medulloblastoma, glioma, pineal astrocytoma, pilocytic astrocytoma, diffuse astrocytoma, anaplastic astrocytoma, pituitary adenoma, etc.), retinoblastoma, skin cancer (e.g., basal cell carcinoma, malignant melanoma, etc.), sarcoma (e.g., rhabdomyosarcoma, leiomyosarcoma, soft tissue sarcoma, etc.), malignant bone tumor, urinary bladder cancer, blood cancer (e.g., multiple myeloma, leukemia, malignant lymphoma, Hodgkin's disease, chronic myeloproliferative disorder, etc.), cancer unknown primary etc.], a cancer growth inhibitor, a cancer metastasis inhibitor, an apoptosis promoter and the like. Among these, the cocrystal of the present invention is effective, for example, for brain tumor, skin cancer, lung cancer, pancreatic cancer, cancer of the bile duct, prostate cancer, esophagus cancer, gastric cancer, colorectal cancer, sarcoma and breast cancer. Especially, the cocrystal of the present invention is effective for glioma, medulloblastoma, basal cell tumor, small cell lung cancer, pancreatic cancer, cancer of the bile duct, prostate cancer, esophagus cancer, gastric cancer, colorectal cancer, rhabdomyosarcoma and breast cancer.

The cocrystal of the present invention can be administered orally or parenterally as it is or in a mixture with a pharmacologically acceptable carrier.

The dosage form of the cocrystal of the present invention for oral administration is, for example, tablet (including sugar-coated tablet, film-coated tablet), pill, granule, powder, capsule (including soft capsule, microcapsule), syrup, emulsion, suspension and the like, and the dosage form for parenteral administration is, for example, injection, injecting agent, instillation, suppository and the like. In addition, it is effective to make a sustained release preparation by combining the cocrystal with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester etc.).

As a method for producing the cocrystal of the present invention in the above-mentioned dosage form, a known production method generally used in the pertinent field can be employed. When the above-mentioned dosage form is produced, suitable amounts of additives such as excipient, binder, disintegrant, lubricant, sweetening agent, surfactant, suspending agent, emulsifier and the like, generally used in the pharmaceutical field, are appropriately added as necessary for production.

When the cocrystal of the present invention is prepared into a tablet, for example, it can be produced by adding an excipient, a binder, a disintegrant, a lubricant and the like, and when a pill or a granule is to be prepared, it can be produced by adding an excipient, a binder, a disintegrant and the like. When a powder or a capsule is to be prepared, it can be produced by adding an excipient and the like, when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, sucrose, microcrystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the cocrystal of the present invention is produced in the above-mentioned dosage form, a suitable amount of a colorant, a preservative, an aromatic, a corrigent, a stabilizer, a thickening agent and the like typically used in the field of preparation can be added on demand.

As the injection, intravenous injection as well as subcutaneous injection, intracutaneous injection, intramuscular injection, instillation and the like are mentioned, and as the sustained release preparation, an iontophoresis transdermal agent and the like are mentioned.

Such injections are prepared by methods known per se, or by dissolving, suspending or emulsifying the cocrystal of the present invention in a sterilized aqueous or oily liquid. As an aqueous liquid for injection, physiological saline, isotonic solutions containing glucose or other auxiliary drugs (e.g., D-sorbitol, D-mannitol, sodium chloride and the like) and the like can be mentioned, and they can be used in combination with suitable solubilizing agents, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like can be mentioned, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like can be blended. A prepared injection is generally filled in an ampoule.

While the content of the cocrystal of the present invention in the pharmaceutical agent of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the pharmaceutical agent of the present invention varies depending on the form of the pharmaceutical preparation, it is generally about 1 to 99.9 wt %, preferably about 10 to 90 wt %, relative to the entire preparation.

The cocrystal of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg) is about 1 to 1000 mg, preferably about 3 to 300 mg, more preferably about 10 to 200 mg, as an active ingredient (6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide), which can be given in a single administration or administered in 2 or 3 portions a day.

When the cocrystal of the present invention is administered parenterally, it is generally administered in the form of a liquid (e.g., injection). While the dose varies depending on the subject of administration, target organ, symptom, administration method and the like, it is, for example, generally about 0.01 mg to about 100 mg, preferably about 0.01 to about 50 mg, more preferably about 0.01 to about 20 mg as the active ingredient (6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide), in the form of an injection, relative to 1 kg body weight, which is preferably given by intravenous injection.

EXAMPLES

The present invention is described in more detail in the following by referring to Examples and Formulation Examples. However, the present invention is not limited by the following Examples and Formulation Examples, and can be practiced with appropriate modifications as long as it is compatible with the above-mentioned and the following gist. All of such modifications are encompassed in the technical scope of the present invention.

In the Examples, room temperature means about 15-30° C.

Powder X-ray diffraction measurement was performed using Cu—Kα radiation and measured by horizontal multipurpose X-ray diffraction system Ultima IV manufactured by Rigaku Corporation. Differential scanning calorimetric or thermogravimetric measurement was performed using DSC1/700/903-2 manufactured by Mettler Toledo or TGA/DSC1/LF/629-2 manufactured by Mettler Toledo and measured at temperature rise rate 5° C./min. Infrared spectrum was measured using Fourier transform infrared spectrophotometer Shimadzu IR Prestige-21 manufactured by Shimadzu Corporation and mounting Dura Sample IR II manufactured by Smiths Detection and by a total reflection method absorption measurement method at resolution 4 cm$^{-1}$. Raman spectroscopy was measured using RXN2 manufactured by Kaiser Optical Systems and a laser light source at excitation wavelength 1064 nm. Single crystal X-ray diffraction was measured using Cu—Kα radiation and curved imaging plate single crystal automatic X-ray structure analyzer R-AXIS RAPID II manufactured by Rigaku Corporation. Initial phase was determined by the direct method and the structure was refined by SHELXL-97. As the solubility, the concentration of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide in distilled water, the Japanese Pharmacopoeia 1st fluid for dissolution test, Fasted State Simulated Intestinal Fluid (FaSSIF) or Fed State Simulated Intestinal Fluid (FeSSIF) after shaking each crystal at 37° C. for 24 hr was used. Intrinsic dissolution rate measurement was evaluated using a compression-molded disc of a crystal powder alone and in 20 mmoL/L sodium phosphate buffer (pH 6.8) containing 0.2% (w/v) sodium lauryl sulfate and by a rotating disc method (rotating speed: 100 rpm). Dissolution test was performed using a powder obtained by physically mixing a crystal powder and lactose in the same weight as the crystal powder and evaluated in Fasted State Simulated Intestinal Fluid (FaSSIF) at 37° C. by a rotating paddle method (paddle rotating speed: 50 rpm). The drug concentration of a solution was determined by liquid chromatography using Alliance HPLC system e2695 and detector 2789 manufactured by Waters (separation column: YMCPackPro C18 4.6 mmϕ×150 mm, temperature: 40° C., mobile phase: 20 mmol/L sodium phosphate buffer (pH 6.8)/acetonitrile=60/40 (v/v), flow rate: 1 mL/min, ultraviolet absorption detection wavelength: 240 nm). As slurry experiment, a test solvent was added to a crystal powder, the mixture was stirred at about 25° C. for 24 hr in suspension, the obtained residue was collected by filtration, and the crystal form was confirmed by powder X-ray diffraction measurement or Raman spectroscopy. In the recrystallization experiment, crystals were dissolved in ethanol, acetone, 2-propanol, tetrahydrofuran, methyl ethyl ketone, ethyl acetate, isopropyl acetate, anisole or isobutyl acetate at 55° C., filtered through a filter, allowed to cool to 5° C. or allowed to cool to 5° C. after adding n-heptane to the solution, and the crystal form of the obtained precipitate was confirmed by powder X-ray diffraction measurement or Raman spectroscopy.

Other symbols in the present specification mean the following.

JP1: the Japanese Pharmacopoeia 1st fluid for dissolution test
FaSSIF: Fasted State Simulated Intestinal Fluid
FeSSIF: Fed State Simulated Intestinal Fluid
API: 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide Example 1

Cocrystal of API and L-Malic Acid

About 1 g of API anhydride crystal was dissolved in 10 mL of acetone and about 130 mg of L-malic acid was dissolved in about 1 mL of ethanol each at 50° C. and they were blended. The obtained solution was hot filtered while keeping at 50° C. and about 17 mL of n-heptane was added slowly. The obtained solution was allowed to cool to room temperature and the obtained precipitate was collected by filtration and dried at 80° C. under reduced pressure to give a crystal.

Figure 2:
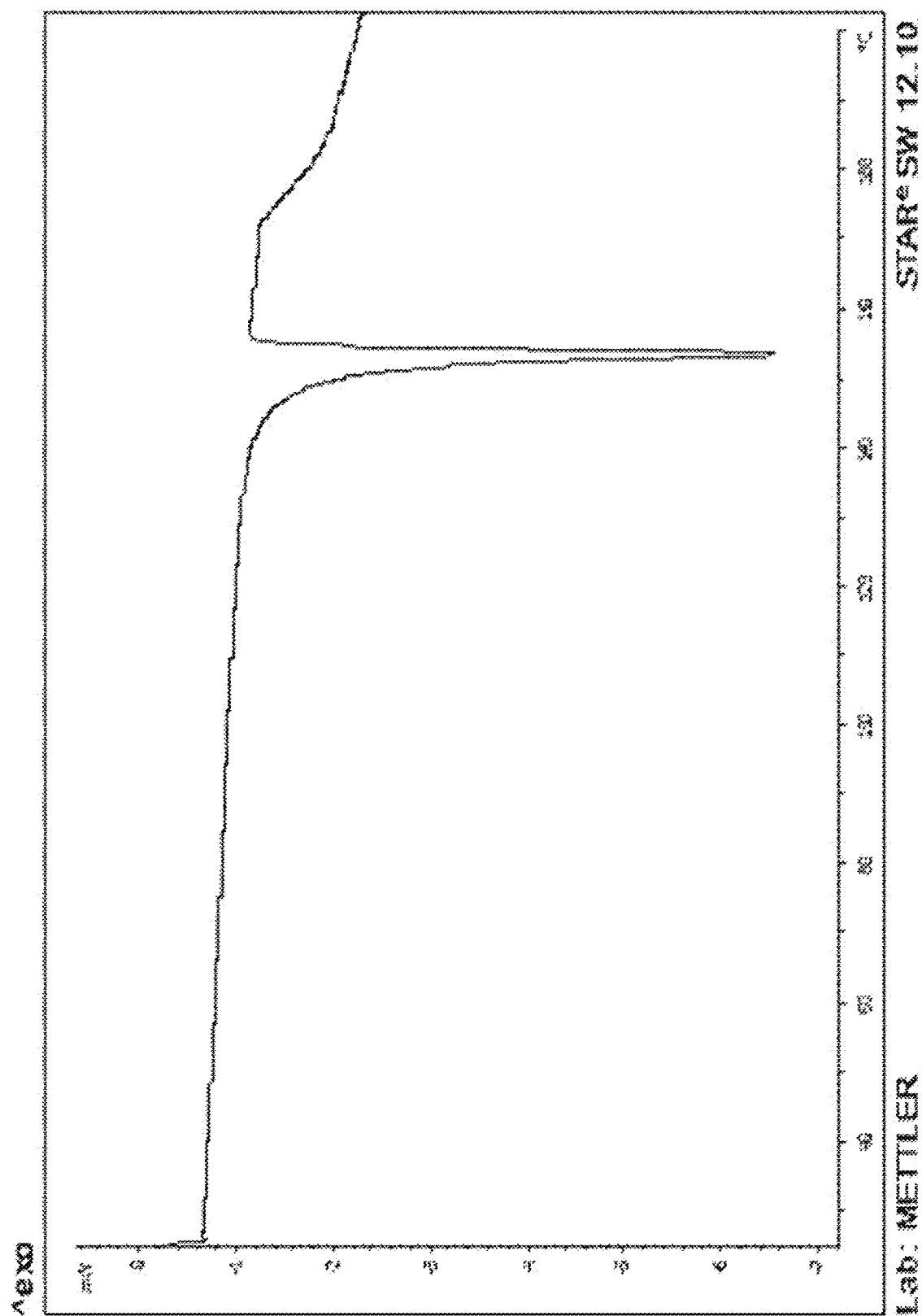
FIG. 2 shows a differential scanning calorimetry curve of a cocrystal of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-malic acid.
Figure 3:
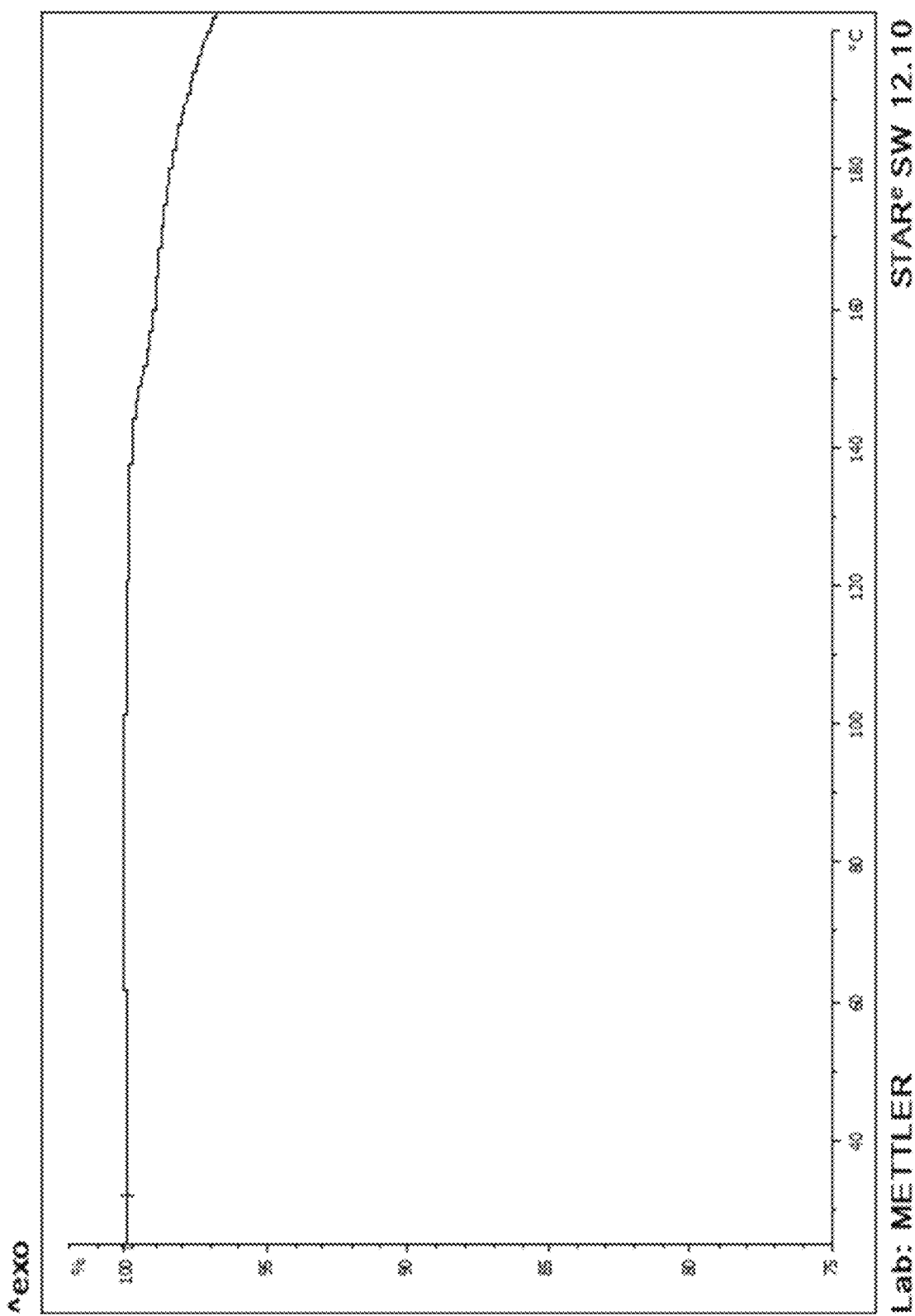
FIG. 3 shows a thermogravimetry curve of a cocrystal of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-malic acid.
Figure 4:
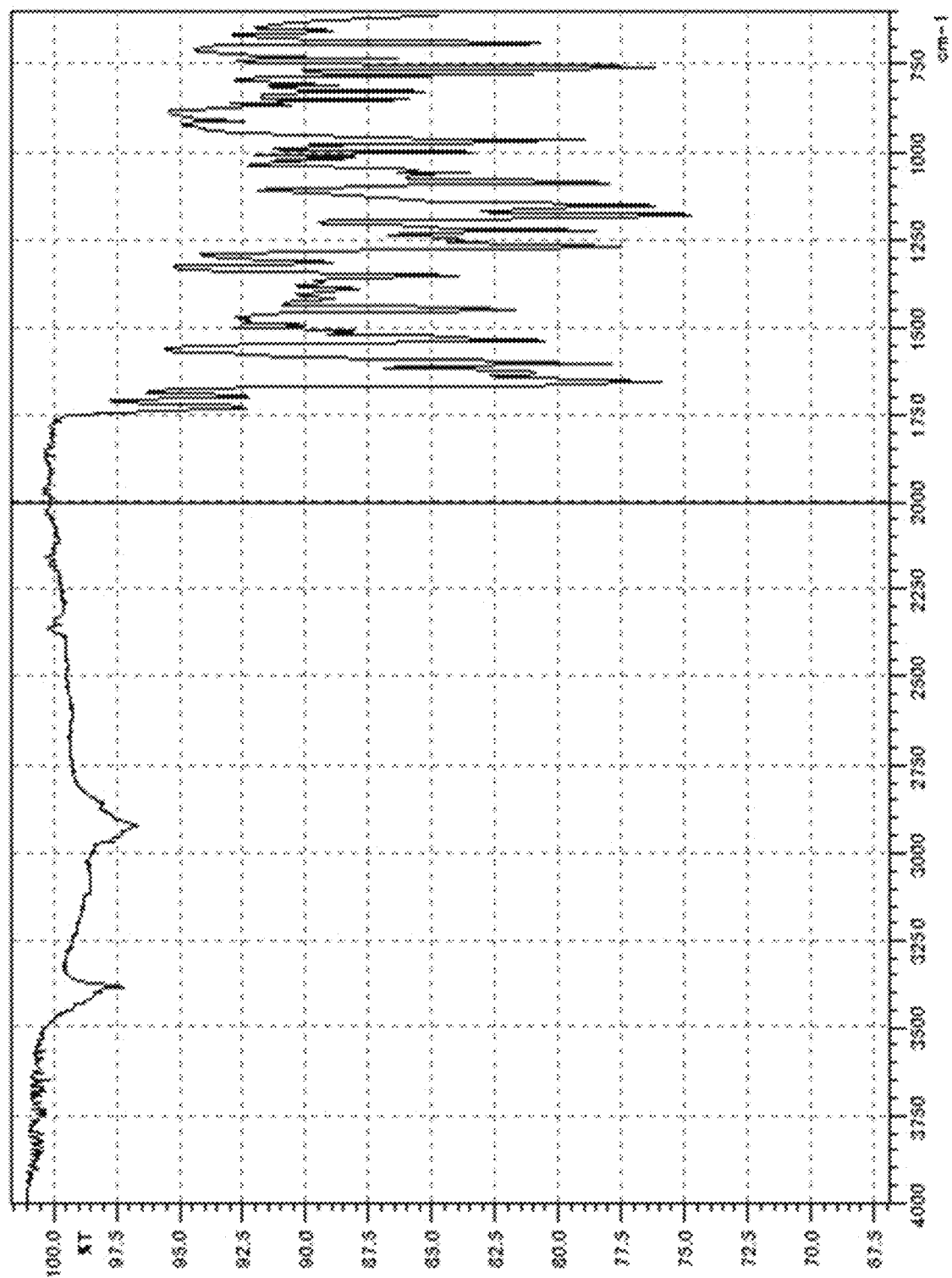
FIG. 4 shows an infrared absorption spectrum of a cocrystal of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-malic acid.
Figure 5:
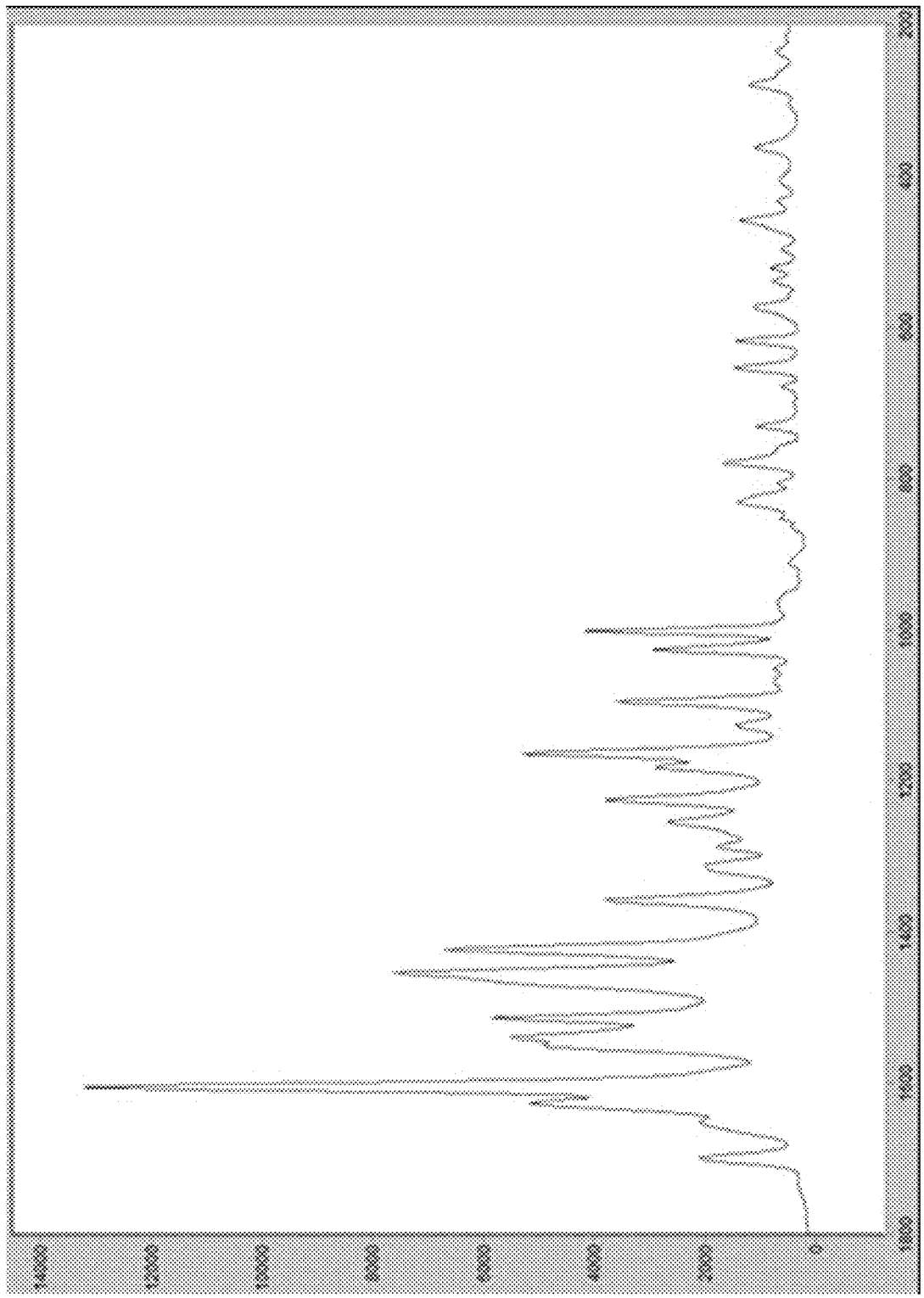
FIG. 5 shows a Raman spectrum of a cocrystal of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-malic acid.

The obtained crystal showed the pattern of FIG. 1 by powder X-ray diffraction measurement and had characteristic peaks at d values of 11.7 angstrom, 10.0 angstrom, 8.6 angstrom, 5.8 angstrom and 4.9 angstrom. In differential scanning calorimetry, peaks associated with melting or decomposition with the apex near 153° C. shown in FIG. 2 was observed. In thermogravimetric measurement, as shown in FIG. 3, a significant weight decrease was not observed up to around the temperature at which the peak was observed in the above-mentioned differential scanning calorimetry, and therefore, it was supported that the crystal was an anhydrous crystal free of a solvent. The obtained crystal showed the infrared absorption spectrum of FIG. 4, and carbonyl stretching vibration derived from carboxylic acid of L-malic acid near 1730 cm$^{-1}$, and therefore, it was supported that L-malic acid in the crystal was in a nonionic state and was a cocrystal. In addition, the obtained crystal showed a characteristic peak near 1625 cm$^{-1}$ in Raman spectroscopy as shown in FIG. 5. The X-ray crystal structure parameter and structure refinement parameter were as shown in Table 1-1. The obtained X-ray crystal structure shows that the obtained crystal was an anhydride crystal constituted of 1 molecule of L-malic acid relative to 2 molecules of API. The interatomic distance between the carbon atom and the oxygen atom in the carboxylic acid of L-malic acid in the obtained X-ray crystal structure was 1.16(1) angstrom and 1.306(7) angstrom, or 1.211(9) angstrom and 1.313(6) angstrom, respectively. From the asymmetry of the carbon atom and oxygen atom in the same carboxylic acid functional group, it was also supported that the L-malic acid in the crystal was in a nonionic state and was a cocrystal.

Example 2

Cocrystal of API and L-Tartaric Acid

About 1 g of API anhydride crystal was dissolved in about 10 mL of methyl ethyl ketone and about 146 mg of L-tartaric acid was dissolved in about 1 mL of ethanol each at 75° C. and they were blended. The obtained solution was hot filtered while keeping at 75° C. and about 9.5 mL of n-heptane was added slowly. The obtained solution was allowed to cool to room temperature and the obtained precipitate was collected by filtration and dried at 80° C. under reduced pressure to give a crystal.

Figure 6:
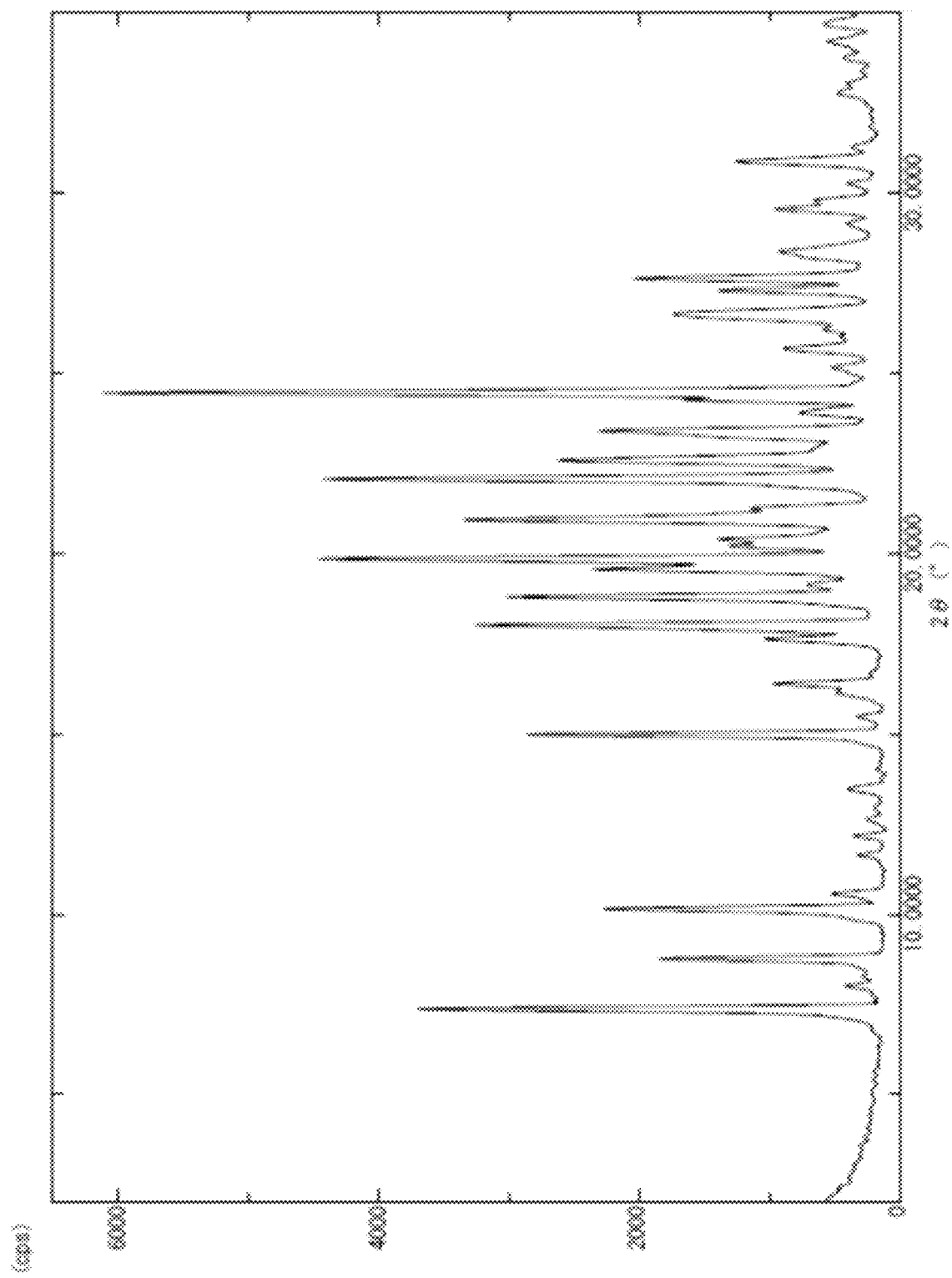
FIG. 6 shows a powder X-ray diffraction pattern of a cocrystal of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-tartaric acid.
Figure 7:
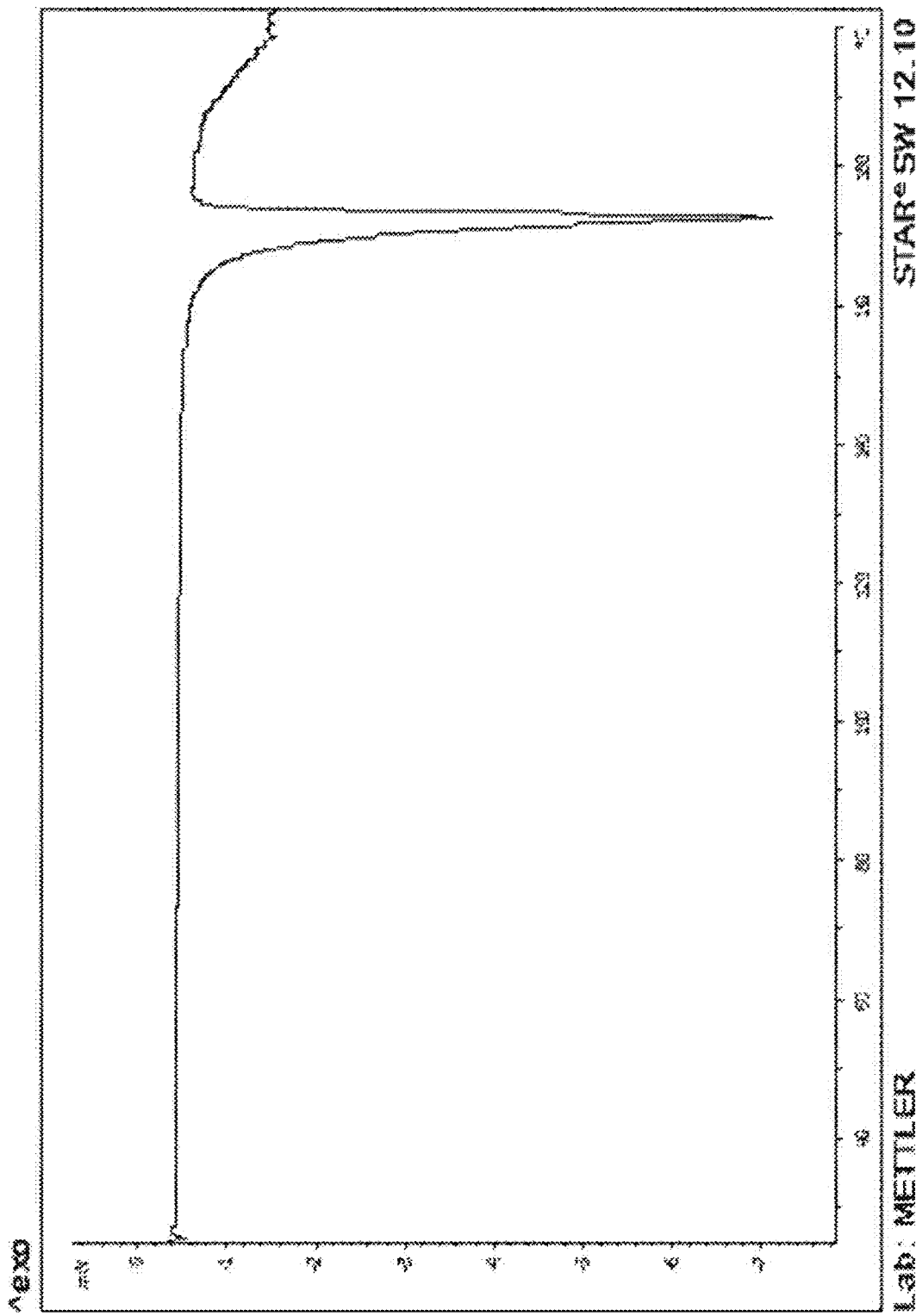
FIG. 7 shows a differential scanning calorimetry curve of a cocrystal of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-tartaric acid.
Figure 8:
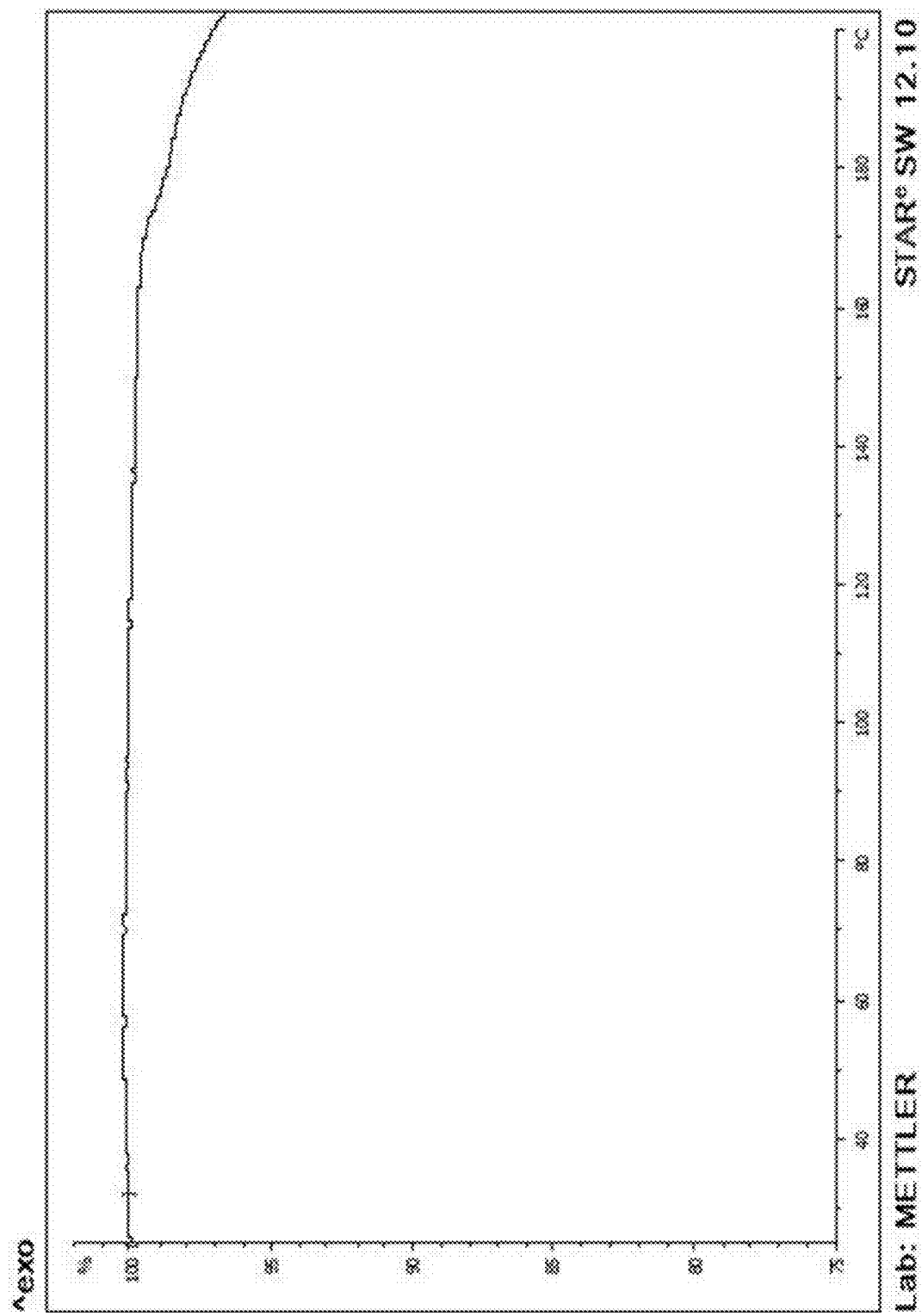
FIG. 8 shows a thermogravimetry curve of a cocrystal of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-tartaric acid.
Figure 9:
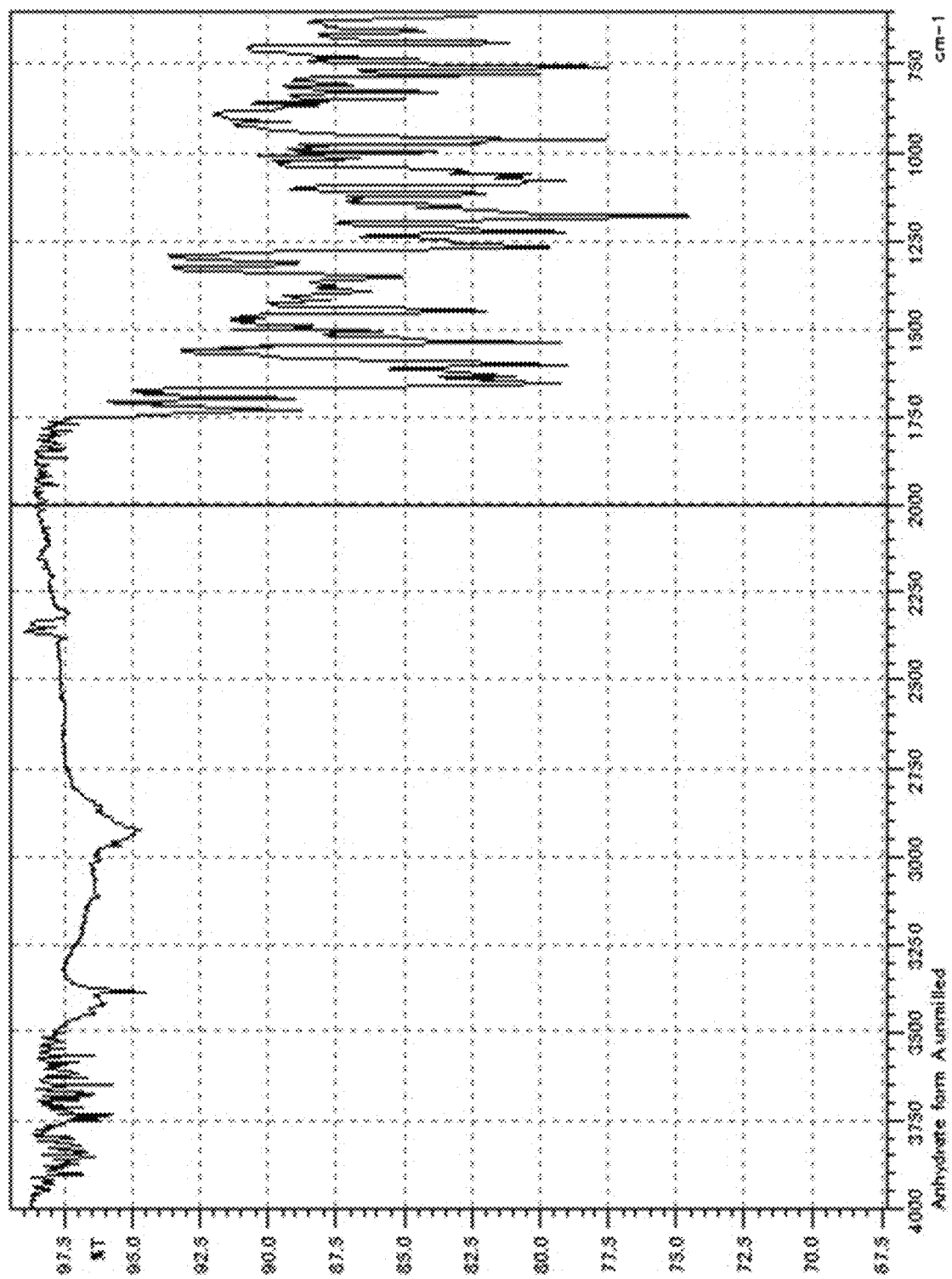
FIG. 9 shows an infrared absorption spectrum of a cocrystal of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-tartaric acid.
Figure 10:
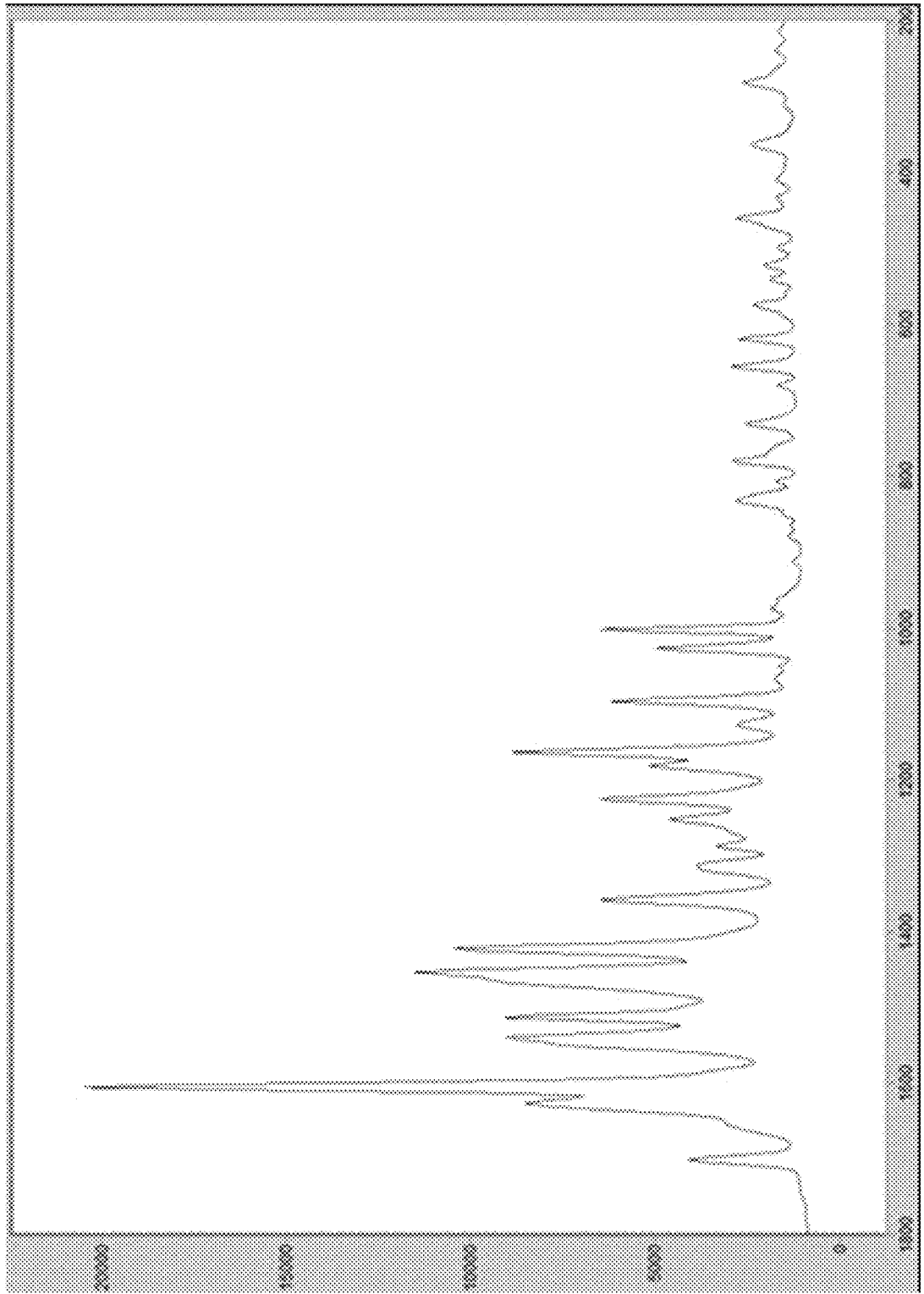
FIG. 10 shows a Raman spectrum of a cocrystal of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-tartaric acid.

The obtained crystal showed the pattern of FIG. 6 by powder X-ray diffraction measurement and had characteristic peaks at d values of 12.0 angstrom, 10.1 angstrom, 8.7 angstrom, 5.9 angstrom and 4.9 angstrom. In differential scanning calorimetry, peaks associated with melting or decomposition with the apex near 170° C. shown in FIG. 7 was observed. In thermogravimetric measurement, as shown in FIG. 8, a significant weight decrease was not observed up to around the temperature at which the peak was observed in the above-mentioned differential scanning calorimetry, and therefore, it was supported that the crystal was an anhydrous crystal free of a solvent. The obtained crystal showed the infrared absorption spectrum of FIG. 9, and carbonyl stretching vibration derived from carboxylic acid of L-tartaric acid near 1734 cm$^{-1}$, and therefore, it was supported that L-tartaric acid in the crystal was in a nonionic state and was a cocrystal. In addition, the obtained crystal showed a characteristic peak near 1625 cm$^{-1}$ in Raman spectroscopy as shown in FIG. 10. The X-ray crystal structure parameter and structure refinement parameter were as shown in Table 1-1. The obtained X-ray crystal structure shows that the obtained crystal was an anhydride crystal constituted of 1 molecule of L-tartaric acid relative to 2 molecules of API. The interatomic distance between the carbon atom and the oxygen atom in the carboxylic acid of L-tartaric acid in the obtained X-ray crystal structure was 1.230(6) angstrom and 1.313(4) angstrom, or 1.219(5) angstrom and 1.323(4) angstrom, respectively. From the asymmetry of the carbon atom and oxygen atom in the same carboxylic acid functional group, it was also supported that the L-tartaric acid in the crystal was in a nonionic state and was a cocrystal.

TABLE 1-1

X-ray crystal structure parameter and structure refinement parameter of cocrystal of API and L-malic acid or L-tartaric acid

|  |  | cocrystal with L- | cocrystal with L- |
|---|---|---|---|
| molecular formula |  | $C_{28}H_{31}F_3N_4O_6 \cdot 0.5C_4H_6O_5$ | $C_{28}H_{31}F_3N_4O_6 \cdot 0.5C_4H_6O_6$ |
| molecular weight |  | 643.62 | 651.62 |
| measurement |  | 100 | 100 |
| crystal system |  | triclinic | triclinic |
| space group |  | P1 | P1 |
| lattice | a (Å) | 10.3587(2) | 10.26620(19) |
| constant | b (Å) | 12.2902(3) | 12.2121(2) |
|  | c (Å) | 13.2739(3) | 13.5689(2) |
|  | α (°) | 115.830(8) | 116.5660(13) |
|  | β (°) | 97.359(7) | 97.2384(10) |
|  | γ (°) | 99.309(7) | 98.6225(8) |
|  | V (Å³) | 1463.05(15) | 1468.07(5) |
| Z |  | 2 | 2 |
| R value [I > 2 σ (I)] |  | 0.0654 | 0.0428 |

Furthermore, using other crystal in the same lot as the crystal from which the data in the above-mentioned Table 1-1 was obtained, measurement and analysis were performed under the same conditions. The X-ray crystal structure parameter and structure refinement parameter obtained when the structure was refined in a model reflecting the two kinds of packing modes of L-malic acid in crystals by arranging a model of hydrogen atoms of methyl groups by differential Fourier synthesis are as shown in Table 1-2.

TABLE 1-2

X-ray crystal structure parameter and structure refinement parameter of cocrystal of API and L-malic acid or L-tartaric acid

|  |  | cocrystal with L- | cocrystal with L- |
|---|---|---|---|
| molecular formula |  | $C_{28}H_{31}F_3N_4O_6 \cdot 0.5C_4H_6O_5$ | $C_{28}H_{31}F_3N_4O_6 \cdot 0.5C_4H_6O_6$ |
| molecular weight |  | 643.62 | 651.62 |
| measurement |  | 100 | 100 |
| crystal system |  | triclinic | triclinic |
| space group |  | P1 | P1 |
| lattice |  | 10.3561(3) | 10.26620(19) |
| constant | a (Å) | 12.3038(3) | 12.2121(2) |
|  | b (Å) |  |  |
|  | c (Å) | 13.2703(4) | 13.5689(2) |
|  | α (°) | 115.840(8) | 116.5660(13) |
|  | β (°) | 97.331(7) | 97.2384(10) |
|  | γ (°) | 99.302(7) | 98.6225(8) |
|  | V (Å³) | 1464.00(15) | 1468.07(5) |
| Z |  | 2 | 2 |
| R value [I > 2 σ (I)] |  | 0.0428 | 0.0426 |

Figure 11:
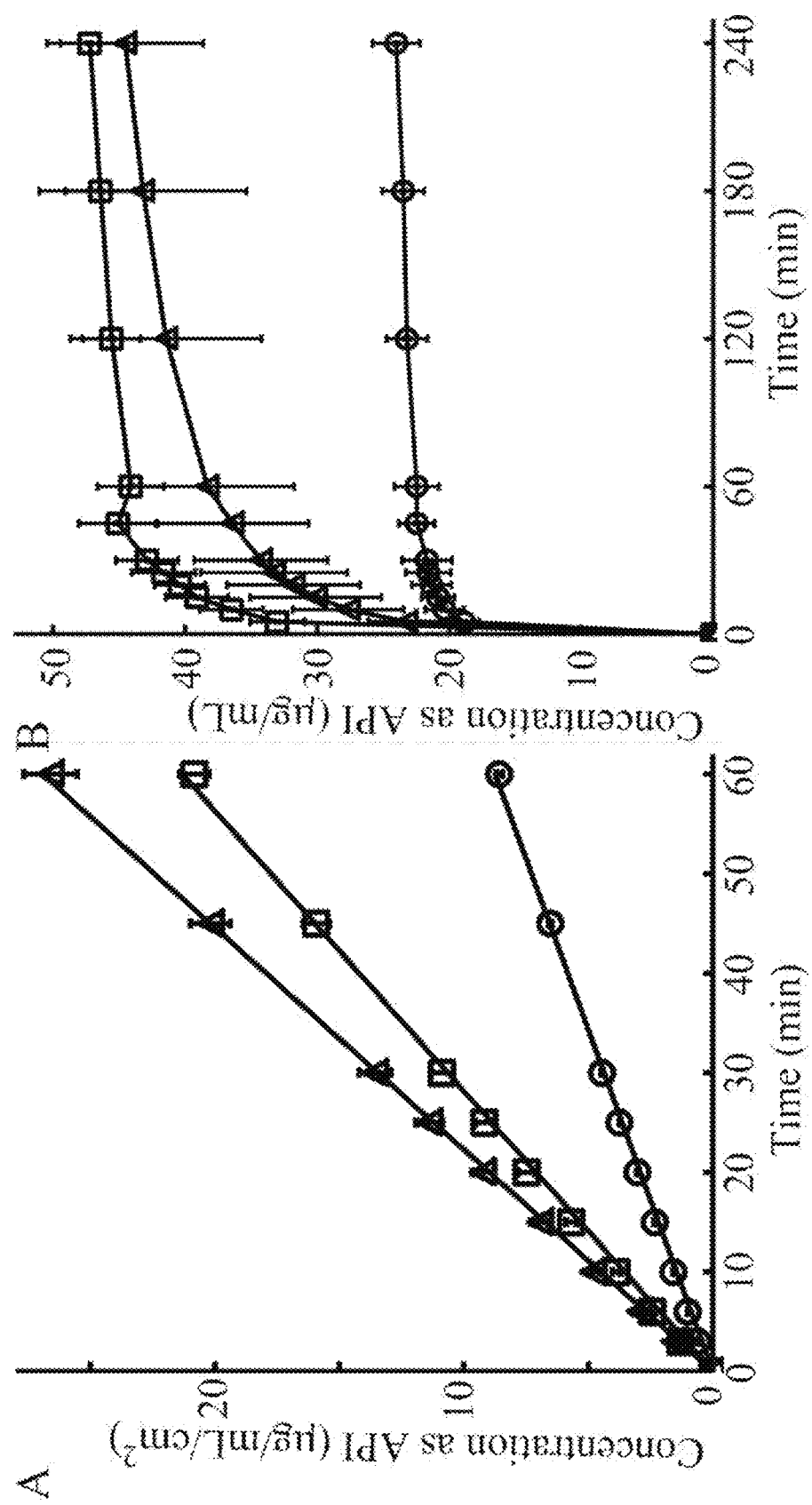
FIG. 11 shows intrinsic dissolution rate (A) and elution profile (B) of an anhydride crystal (round) of free form of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide, a cocrystal (trigonal) of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-malic acid and a cocrystal (square) of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and L-tartaric acid.

The solubilities of a cocrystal of API and L-malic acid or a cocrystal of API and L-tartaric acid and an anhydrous crystal of a free form of API are shown in Table 2, and the intrinsic dissolution rate and the results of dissolution test are shown in FIG. 11. The cocrystals all showed high solubility as compared to the anhydrous crystal of a free form of API.

TABLE 2

Solubility of anhydrous crystal of free form of API, cocrystal of API and L-malic acid and cocrystal of API and L-tartaric acid in each aqueous solution

| | solubility (μg/mL) | | |
|---|---|---|---|
| | anhydrous crystal of free form | cocrystal with L-malic acid | cocrystal with L-tartaric acid |
| distilled water | 21.5 ± 0.5 | 37.6 ± 2.7 | 36.2 ± 4.1 |
| JP1 | 20.6 ± 0.4 | 38.7 ± 0.2 | 45.0 ± 7.6 |
| FaSSIF | 23.9 ± 0.1 | 76.6 ± 1.2 | 61.0 ± 7.9 |
| FeSSIF | 88.7 ± 0.7 | 541.0 ± 4.9 | 569.4 ± 6.6 |

A cocrystal of API and L-malic acid or a cocrystal of API and L-tartaric acid and an anhydrous crystal of a free form of API were subjected to a slurry experiment in each solvent, and the results of the crystal form of the residue are shown in Table 3. In addition, the crystal form of the precipitate obtained by recrystallization from each organic solvent was examined and the results are shown in Table 4. None of the cocrystals showed a solvate of cocrystal, and it was suggested that a solvate was not formed easily as compared to the anhydrous crystal of a free form of API.

TABLE 3

Crystal form of residue after slurry experiment in each solvent

| | cocrystal with L-malic acid | cocrystal with L-tartaric acid | anhydrous crystal of free form |
|---|---|---|---|
| ethanol | cocrystal * | cocrystal * + free form (solvate) | free form (solvate) |
| acetone | cocrystal * | cocrystal * | free form (solvate) |
| 2-propanol | cocrystal * | cocrystal* + free form (solvate) | free form (solvate) |
| tetrahydrofuran | free form (solvate) | cocrystal* + free form (solvate) | free form (solvate) |
| methyl ethyl ketone | cocrystal* + free form (solvate) | cocrystal* + free form (solvate) | free form (solvate) |
| ethyl acetate | cocrystal* + free form (solvate) | cocrystal* + free form (solvate) | free form (solvate) |
| anisole | free form (solvate) | cocrystal* + free form (solvate) | free form (solvate) |
| distilled water | cocrystal* + free form (solvate) | cocrystal* + free form (solvate) | free form (solvate) |

Preparation Example 1

A medicament containing the cocrystal of the present invention as an active ingredient can be produced, for example, according to the following formulations.

1. Capsule

| | |
|---|---|
| (1) cocrystal obtained in Example 1 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. The remaining (4) is added and the whole is encapsulated in a gelatin capsule.

2. Tablet

| | |
|---|---|
| (1) cocrystal obtained in Example 1 | 40 mg |
| (2) lactose | 58 mg |
| (3) cornstarch | 18 mg |

TABLE 4

Crystal form of precipitate obtained from each solvent by recrystallization experiment

| | cocrystal with L-malic acid | cocrystal with L-tartaric acid | anhydrous crystal of free form |
|---|---|---|---|
| ethanol | free form (solvate) | free form (solvate) | free form (solvate) |
| acetone | free form (solvate) | free form (solvate) | free form (solvate) |
| 2-propanol | no precipitate | cocrystal * | free form (solvate) |
| tetrahydrofuran | free form (solvate) | free form (solvate) | free form (solvate) |
| methyl ethyl ketone | free form (solvate) | free form (solvate) | free form (solvate) |
| ethyl acetate | free form (solvate) | free form (solvate) | free form (solvate) |
| anisole | no precipitate | no precipitate | free form (solvate) |
| isopropyl acetate | free form (solvate) | free form (solvate) | free form (solvate) |
| isobutyl acetate | cocrystal* + free form (solvate) | cocrystal * | free form (solvate) |
| ethanol/n-heptane | free form (solvate) | free form (solvate) | free form (solvate) |
| acetone/n-heptane | free form (solvate) | cocrystal* + free form (solvate) | free form (solvate) |
| 2-propanol/n-heptane | cocrystal * | cocrystal* | free form (solvate) |
| tetrahydrofuran/n-heptane | cocrystal + free form (solvate) | cocrystal * | free form (solvate) |
| methyl ethyl ketone/n-heptane | cocrystal + free form (solvate) | cocrystal * | free form (solvate) |
| ethyl acetate/n-heptane | free form (solvate) | cocrystal * + free form (solvate) | free form (solvate) |
| anisole/n-heptane | free form (solvate) | free form (solvate) | free form (solvate) |
| isopropyl acetate/n-heptane | cocrystal* + free form (solvate) | cocrystal * | free form (solvate) |
| isobutyl acetate/n-heptane | free form (solvate) | cocrystal * | free form (solvate) |

* All of the obtained cocrystals were the same as the crystal form used.

| | |
|---|---|
| (4) microcrystalline cellulose | 3.5 mg |
| (5) magnesium stearate | 0.5 mg |
| 1 tablet | 120 mg |

(1), (2), (3), ⅔ of (4) and ½ of (5) are blended and granulated. The remaining (4) and (5) are added to the granule and compression formed into a tablet.

Preparation Example 2

The cocrystal (50 mg) obtained in Example 1 was dissolved in the Japanese Pharmacopoeia distilled water (50 ml) for injection. Then, the Japanese Pharmacopoeia distilled water for injection is added to 100 ml. This solution was filtered under sterilization conditions, and the solution (1 ml) was taken, filled in an injection vial under sterile conditions, freeze-dried and tightly sealed.

INDUSTRIAL APPLICABILITY

According to the present invention, a cocrystal having improved solubility and/or supressing easy formation of a solvate can be obtained to improve the effect of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide useful as a prophylactic or therapeutic agent for cancer.

The invention claimed is:

1. A cocrystal of
   (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and
   (2) L-malic acid or L-tartaric acid.

2. The cocrystal according to claim 1 that is a cocrystal of
   (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and
   (2) L-malic acid.

3. The cocrystal according to claim 2, characterized by a powder X-ray diffraction pattern comprising characteristic peaks at d values of 11.7±0.2, 10.0±0.2, and 8.6±0.2 angstroms.

4. The cocrystal according to claim 1 that is a cocrystal of
   (1) 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide and
   (2) L-tartaric acid.

5. The cocrystal according to claim 4, characterized by a powder X-ray diffraction pattern comprising characteristic peaks at d values of 12.0±0.2, 10.1±0.2 and 8.7±0.2 angstroms.

6. A pharmaceutical composition comprising the cocrystal according to claim 1.

7. The pharmaceutical composition according to claim 6 that is a Smo inhibitor.

8. The pharmaceutical composition according to claim 6 that is a prophylactic and/or therapeutic agent for cancer.

9. A method for inhibiting Smo in a mammal, comprising administering an effective amount of the cocrystal according to claim 1 to the mammal.

10. A method for treating cancer in a mammal, comprising administering an effective amount of the cocrystal according to claim 1 to the mammal.

11. The method according to claim 10, wherein the cancer is selected from one or more of colorectal cancer, lung cancer, mesothelioma, pancreatic cancer, pharyngeal cancer, laryngeal cancer, esophageal cancer, gastric cancer, duodenal cancer, small intestinal cancer, breast cancer, ovarian cancer, testicular cancer, prostate cancer, liver cancer, thyroid cancer, kidney cancer, uterus cancer, brain tumor, retinoblastoma, skin cancer, sarcoma, malignant bone tumor, urinary bladder cancer, and blood cancer.

12. The method of claim 10, wherein the cancer is selected from one or more of glioma, medulloblastoma, basal cell tumor, small cell lung cancer, pancreatic cancer, cancer of the bile duct, prostate cancer, esophagus cancer, gastric cancer, colorectal cancer, rhabdomyosarcoma, and breast cancer.

* * * * *